(12) United States Patent
Geddes

(10) Patent No.: US 8,987,004 B2
(45) Date of Patent: *Mar. 24, 2015

(54) NANOSTRUCTURES FOR POLARIZED IMAGING AND RECEPTOR/LIGAN QUANTIZATION: BREAKING THE DIFFRACTION LIMIT FOR IMAGING

(75) Inventor: Chris D. Geddes, Bel-Air, MD (US)

(73) Assignee: University of Maryland, Baltimore County, Baltimore, MD (US)

(*) Notice: Subject to any disclaimer, the term of this patent is extended or adjusted under 35 U.S.C. 154(b) by 1935 days.

This patent is subject to a terminal disclaimer.

(21) Appl. No.: 11/997,778

(22) PCT Filed: Aug. 2, 2006

(86) PCT No.: PCT/US2006/030268
§ 371 (c)(1),
(2), (4) Date: Aug. 28, 2009

(87) PCT Pub. No.: WO2008/048221
PCT Pub. Date: Apr. 24, 2008

(65) Prior Publication Data
US 2009/0325199 A1    Dec. 31, 2009

Related U.S. Application Data

(60) Provisional application No. 60/704,660, filed on Aug. 2, 2005.

(51) Int. Cl.
G01N 33/553   (2006.01)
G01N 33/58    (2006.01)
G01N 33/543   (2006.01)

(52) U.S. Cl.
CPC ........ *G01N 33/587* (2013.01); *G01N 33/54346* (2013.01); *G01N 33/54373* (2013.01); *Y10S 436/805* (2013.01)

USPC .......... 436/532; 436/524; 436/164; 436/805; 436/64; 435/7.23

(58) Field of Classification Search
None
See application file for complete search history.

(56) References Cited

U.S. PATENT DOCUMENTS 4,174,952 A * 11/1979 Cannell et al. ............... 436/534
4,313,734 A *  2/1982 Leuvering ..................... 436/525
(Continued)

FOREIGN PATENT DOCUMENTS

WO        89/09408      10/1989
WO        WO97/40181 A  10/1997
(Continued)

OTHER PUBLICATIONS

Aslan Kadir et al: "Angular-dependent polarization-based plasmon light scattering for bioaffinity sensing" Applied Physics Letters, AIP, American Institute of Physics, Melville, NY, US, vol. 87, No. 23, Dec. 1, 2005.

(Continued)

*Primary Examiner* — Chris L Chin
(74) *Attorney, Agent, or Firm* — Marianne Fuierer; Moore & Van Allen, PLLC

(57) ABSTRACT

The present invention relates to affinity biosensing using polarization of light scattering of aggregated noble metallic nanostructures to determine concentration of an analyte in a test sample. This new sensing system utilizes the changes in polarized plasmonic scattering from nanostructures as the nanostructures aggregate due to binding of the analyte to a binding partner attached to the surface of the metallic nanostructure.

20 Claims, 8 Drawing Sheets

(56) References Cited

U.S. PATENT DOCUMENTS

| | | | |
|---|---|---|---|
| 4,444,879 A * | 4/1984 | Foster et al. | 435/7.95 |
| 5,017,009 A | 5/1991 | Schutt et al. | |
| 5,449,918 A | 9/1995 | Krull et al. | |
| 5,866,433 A | 2/1999 | Schalkhammer et al. | |
| 6,180,415 B1 | 1/2001 | Schultz | |
| 7,253,452 B2 | 8/2007 | Steckel et al. | |
| 7,348,182 B2 | 3/2008 | Martin et al. | |
| 7,351,590 B2 | 4/2008 | Martin | |
| 7,718,445 B2 | 5/2010 | Martin | |
| 2001/0002315 A1 * | 5/2001 | Schultz et al. | 436/172 |
| 2001/0053521 A1 * | 12/2001 | Kreimer et al. | 435/6 |
| 2003/0228682 A1 | 12/2003 | Lakowicz et al. | |
| 2004/0009540 A1 | 1/2004 | Soohoo et al. | |
| 2004/0160606 A1 | 8/2004 | Lakowicz et al. | |
| 2005/0019842 A1 * | 1/2005 | Prober et al. | 435/7.9 |
| 2005/0136258 A1 | 6/2005 | Nie et al. | |
| 2006/0147927 A1 | 7/2006 | Geddes et al. | |
| 2006/0148104 A1 * | 7/2006 | Marini et al. | 436/524 |
| 2007/0269826 A1 | 11/2007 | Geddes | |
| 2008/0096281 A1 | 4/2008 | Geddes et al. | |
| 2009/0022766 A1 | 1/2009 | Geddes | |

FOREIGN PATENT DOCUMENTS

| | | |
|---|---|---|
| WO | WO 2004/024191 | 3/2004 |
| WO | WO 2006/074130 | 7/2006 |
| WO | WO 2006/137945 | 12/2006 |
| WO | WO 2006/138698 | 12/2006 |
| WO | WO 2007/053201 | 5/2007 |
| WO | WO 2007/095527 | 8/2007 |

OTHER PUBLICATIONS

Aslan K et al: Plasmon light scattering in biology and medicine: new sensing approaches, visions and perspectives Current Opinions in Chemical Biology, Current Biology Ltd, London, GB, vol. 9, No. 5, Oct. 1, 2005.

Bryant, G.; Thomas, J.C. Improved Particle Size Distribution Measurements Using Multiangle Dynamic Light Scattering. *Langmuir* 1995, 11, 2480-2485.

Yguerabide, J.; Yguerabide, E. Light Scattering Submicroscopic Particle as Highly Fluorescent Analogs and their Use as Tracer Labels in Clinical and Biological Applications. *Anal. Biochem.* 1998, 262, 137-156.

Yguerabide, J.; Yguerabide, E. Light Scattering Submicroscopic Particle as Highly Fluorescent Analogs and their Use as Tracer Labels in Clinical and Biological Applications: Experimental Characterization *Anal. Biochem.* 1998, 262, 157-176.

Aslan, K.; Lakowicz, J. R.; Geddes, C. D. Tunable Plasmonic Glucose Sensing Based on the Dissociation of Con A-aggregated Dextram-coated Gold Colloids. *Anal. Chem.Acta.* 2004, 517, 139-144.

Aslan, K.; Lakowicz, J. R.; Geddes, C. D. Nanogold-plasmon resonance-based Glucose Sensing. *Anal. Biochem.* 2004, 330, 145-155.

Reynolds, R. A.; Mirkin, C. A.; Letsinger, R. L. Homogenous Nanoparticle-based Quantitative Colorimetric Detection of Oligonucleotides. *J. Am. Chem. Soc.* 2000, 122, 3795-3796.

Elghanian, R.; Storhoff, J.J.; Mucic, R.C.; Letsinger, R.L.; Mirkin, C.A. Selective Colorimetric Detection of Polynucleotides Based on the Distance-Dependant Optical Properties of Gold Nanoparticles. *Science* 1997, 277, 1078-1081.

Sastry, M.; Lala, N.; Patil, V.; Chavan, S.P.; Chittiboyina, A.G. Optical Absorption Sutdy of the Biotin-Avidin Interaction on Colloidal Silver and Gold Particles. *Langmuir* 1998, 14, 4138-4142.

Cobbe, S.; Connolly, S.; Ryan, D.; Nagle, L.; Eritja, R.; Fitzmaurice, D. DNA-Controlled Assembly of Protein-Modified Gold Nanocrystals. *J. Phys. Chem. B* 2003, 107, 470-477.

Nath, N.; Chilkoti, A. A Colormetric Gold Nanoparticle Sensor to Interrogate Biomolecular Interactions in Real Time on a Surface. *Anal. Chem.* 2002, 74, 504-509.

Souza, G.R.; Miller, J.H. Oligonucleotide Detection Using Angle-Dependent Light Scattering and Fractal Dimension Analysis of Gold-DNA Aggregates. *J. Am. Chem. Soc.* 2001, 123, 6734-6735.

Mie, G, Contributions to the Optics of Turbid Media, Particularly of Colloidal Metal Solutions. *Ann. Phys.* 1908, 25, 377-445.

Collier, C.P.; Vossmeyer, T.; Heath, J.R. Nanocrystal Superlattices. *Annu. Rev. Phys. Chem.* 1998, 49, 371-404.

Mayes, A. G.; Blyth, J.; Millington, R. B.; Lowe, C. R. Metal Ion-Sensitive Holographic Sensors *Anal. Chem.* 2002, 74, 3649-3657.

Kim, Y.; Johnson, R. C.; Hupp, J. T. Gold Nanoparticle-Based Sensing of "Spectroscopically Silent" Heavy Metal Ions. *Nano Lett.* 2001, 1 (4), 165-167.

E. Hutter and J. H. Fendler, Adv. Mater. (Weinheim, Ger.) 16, 1685 (2004).

K.-H. Su, Q.-H. Wei, X. Zhang, J. J. Mock, D. R. Smith, and S. Schultz, Interparticle Coupling Effects on Plasmon Resonances of Nanogold Particles. *Nano Lett.* 3, 1087 (2003).

K. Aslan, P. Holley, L. Davies, J. R. Lakowicz, and C. D. Geddes, Angular-Ratiometric Plasmon-Resonance Based Light Scattering for Bioaffinity Sensing. *J. Am. Chem. Soc.* 127, 12115 (2005).

Millard, M.; Huang, P.; Brus, L. Silver Nanodisk Growth by Surface Plasmon Enhanced Photoreduction of Absorbed [Ag]. *Nano Lett.* 2003, 3, 1611-1615.

D. A. Stuart, A. J. Haes, C. R. Yonzon, E. M. Hicks, and R. P. Van Duyne, Biological Applications of Localised Surface Plasmonic Phenomenae. IEE. Proc.-Nanobiotechnol. 152, 13 (2005).

Roll, D.; Malicka, J.; Gryczynski, I.; Gryczynski, Z.; Lakowicz, J.R. Metallic Colloid Wavelength-Ratiomestric Scattering Sensors. *Anal. Chem.* 2003, 75, 3108-3113.

Finay, R. Particle Sizing by Quasi-Elastic Light Scattering. *Adv. Colloid Interface Sci.* 1994, 52, 79-143.

\* cited by examiner

NANOSTRUCTURES FOR POLARIZED IMAGING AND RECEPTOR/LIGAN QUANTIZATION: BREAKING THE DIFFRACTION LIMIT FOR IMAGING

CROSS-REFERENCE TO RELATED APPLICATION

The present application claims priority to PCT Application No. PCT/US2006/030268 filed in the U.S. Patent and Trademark Office, PCT Division, on Aug. 2, 2006, which in turn claims priority to U.S. Provisional Patent Application No. 60/704,660 filed on Aug. 2, 2005, the contents of all applications are hereby incorporated by reference herein.

GOVERNMENT RIGHTS IN INVENTION

This invention was made with government support under GM070929 awarded by The National Institutes of Health. The government has certain rights in the invention.

BACKGROUND OF THE INVENTION

1. Field of the Invention

The present invention relates to assays and methods of use, and more particularly, to detection of polarized angular scattering from plasmonic nanostructures for determining concentrations of receptor-ligand binding.

2. Background of the Related Art

Typically, in cellular imaging today, fluorophores or even quantum dots, are used, which either contain some function groups to bind to expressed cellular surface features (receptors) or can even be transfected within the cells. This enables the cells to be readily imaged. However, one particular problem with using fluorophores is there inherent photo instability, where most fluorophores typically photo degrade after about $10^3$ excitation/emission event cycles.

In spectroscopy today, the techniques are typically limited by the wavelength of light for imaging, structures and features less than 1 micron in size being most difficult to see. However, contrary to this, FRET (Fluorescence Resonance Energy Transfer) has earned a well deserved reputation for being able to indirectly image features that are within the Forster Transfer distances of fluorophores, that being, 5 nm. Hence, FRET is widely used to study macromolecular dynamics. However, there is a diffraction limited gap in imaging today because current technology cannot image structures and features in the 10 to 1000 nm size.

Over the last several years, the use of both gold and silver nanoparticles in biological assays has dramatically increased. Nanostructures are far superior to fluorophores in that they don't photodegrade and have "Plasmon Scattering Powers" far greater than the emission of fluorophores. This has been afforded by their very high molar absorption coefficients. In addition to their high absorption cross-sections, nanoparticles of gold and silver are also very efficient scatterers of light. Indeed a noble metal colloid's extinction spectrum is composed of both an absorption and scattering component, which is contrary to how we think of a typical fluorophores extinction spectrum. Subsequently, light scattering by gold and silver nanoparticles can be detected at concentrations as low as $10^{-16}$ M. For example, a 20 nm gold colloid can scatter light at 532 nm, the equivalent intensity as $10^5$ fluorescing fluorescein molecules. In addition, it is well known that the light dependent scattering properties of nanoparticles depend on their size, shape, composition and the refractive index of the suspending medium. However, one property that has been ill explored for biosensing applications is the polarization and intensity of plasmon scatter.

Thus, it would be advantageous to provide a method for using polarized scatter from plasmonic nanostructures for bioassays.

SUMMARY OF THE INVENTION

Surface plasmons are collective oscillations of free electrons at metallic surfaces. These oscillations can give rise to the intense colors of solutions of plasmon resonance nanoparticles and/or intense scattering. When a metallic nanoparticle is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon scatter.

Broadly, the present invention relates to detecting and/or measuring the polarization of scattered plasmonic emissions from the surface of metallic nanostructures or numerous aggregating metallic nanostructures. The scattering effects may be measured at different angles, different wavelength to determine the changes in polarization relative to changes in the distances between metallic nanostructures. The angles of detection may be from about 190 to 250 and from about 100 to about 170, and more preferably, from about 190 to about 220 or from about 140 to about 160. The time of measurement can range from 10 minutes to several hours depending on the length of time required for the specific chemical bonding or affinity reaction between the binding partners of the binding couple.

Notably, metallic nanostructures are far superior to fluorophores in that they do not photodegrade and have far greater emissions than that of fluorophores. Further, nanostructures of gold and silver are very efficient scatterers of light.

The present invention relates to a method of imaging structures and features using the polarization of plasmonic scatter, wherein the structures and features are from about 6 nm up to 1000 nm, more preferably from about 10 nm to about 400 num.

In one aspect, the present invention relates to the use of polarized scattering of plasmonic emissions for cellular imaging and receptor-ligand detection, wherein imaging using polarized scattering has high image contrast relative to the unpolarized scattered light from the cells or tissue.

In another aspect, the present invention relates to a bioassay for measuring concentration of a receptor-ligand binding couple, the method comprising:
 (a) preparing metallic nanostructures being at least partially coated with one member of the binding couple having an affinity for the other member of the binding couple suspected of being in the test sample;
 (b) contacting the metallic nanostructures with a test sample;
 (c) exposing the metallic nanostructures to electromagnetic radiation at a frequency that is scattered by the metallic nanostructures;
 (d) measuring the polarization of scattered light emitted from the metallic nanostructures at a specific angle, wherein the polarization value is decreased as the aggregation of metallic nanostructures increases due to increased binding of the components of the binding couple.

The metallic nanostructures may take the form of metallic islands, colloids, or nanostructures of any geometric shape, such as spherical, triangular, elliptical, rod shape, hexagonal or multifaceted. The metallic element used to fabricate the nanostructures may include any form of metals that support plasmonic emissions, including but not limited to silver, gold, platinum, copper and/or combinations thereof, and more preferably, the metallic material is gold or low density silver. The nanostructures may further be fabricated of a substrate material and subsequently coated with the metallic material wherein the substrate positioned beneath the metallic material may include glass and/or a polymeric material.

In a further aspect, the present invention relates to the use of surface plasmons in a biosensing method for measuring the concentration of an analyte that induces aggregation of metallic nanostructure having a binding receptor for the analyte, the method comprising:

a) providing metallic nanostructure having a binding probe for the analyte, and b) measuring the change in polarization of plasmonic scattered light emitted from metallic nanostructures as aggregation occurs between the metallic nanostructures, wherein aggregation is due to increases in the concentration of analyte binding to the probe and wherein increases in concentration of the analyte binding to the probe correlates to a decrease in polarization.

In yet another aspect, the present invention relates to a bioassay for measuring concentration of receptor-ligand binding, the method comprising:

(a) preparing a metallic sensing structure by attaching a noble metal nanostructure to a ligand having affinity for a receptor on biological tissue;

(b) contacting a sample suspected of containing the biological tissue with the metallic sensing structures;

(c) exposing the sample and metallic sensing structures to electromagnetic radiation at a wavelength that is scattered by the metallic structures;

(d) measuring the polarization of scattered light from metallic structures at a specific angle that provides a polarization value for monitoring aggregation, wherein the polarization value is decreased as binding of the metallic structures to the receptors on the biological tissue increases.

In another aspect, the present invention relates to a biosensing method for measuring concentration of an analyte that induces aggregation of metallic nanostructures, the method comprising:

(a) preparing the metallic nanostructures comprising at least one noble metal and at least partially coated the nanostructures with a binding component having an affinity for the analyte, and wherein the nanostructures are at size that scatters light according to the Rayleigh theory;

(b) exposing the metallic nanostructures with electromagnetic radiation at a frequency that is at least scattered by the metallic nanostructures;

(c) measuring the polarization of scattered light from the metallic nanostructures;

(d) contacting the metallic nanostructures with an analyte that has an affinity for the binding component;

(e) measuring the polarization of scattered light emitted from the metallic nanostructures, wherein the polarization decreases as aggregation increases.

In a still further aspect, the present invention relates to an assay using High Throughput Screening (HTS), the method comprising:

(a) providing a well plate used in HTS systems comprising a multiplicity of wells;

(b) introducing metallic nanostructures into the wells, wherein the metallic nanostructures are coupled to a binding receptor having affinity for a target molecule;

(c) introducing at solution suspected of including the target molecule for binding to the binding receptor;

(d) applying electromagnetic energy; and (e) measuring the change of polarization of plasmonic emissions from the system during a predetermined time period, wherein polarization values decrease as the binding of the target molecule increases.

A further aspect of the present invention, relates to a kit for detecting a target molecule in a sample, the kit comprising a container including metallic particles that are fabricated of a metallic material that generate plasmonic emissions when irradiated with electromagnetic energy, wherein the metallic particles are sized to scatter light and comprise immobilized receptors or probes and wherein the immobilized receptors or probes have an affinity for the target molecule in a test sample.

Other features and advantages of the invention will be apparent from the following detailed description, drawings and claims.

DETAILED DESCRIPTION OF THE INVENTION

Figure 1:
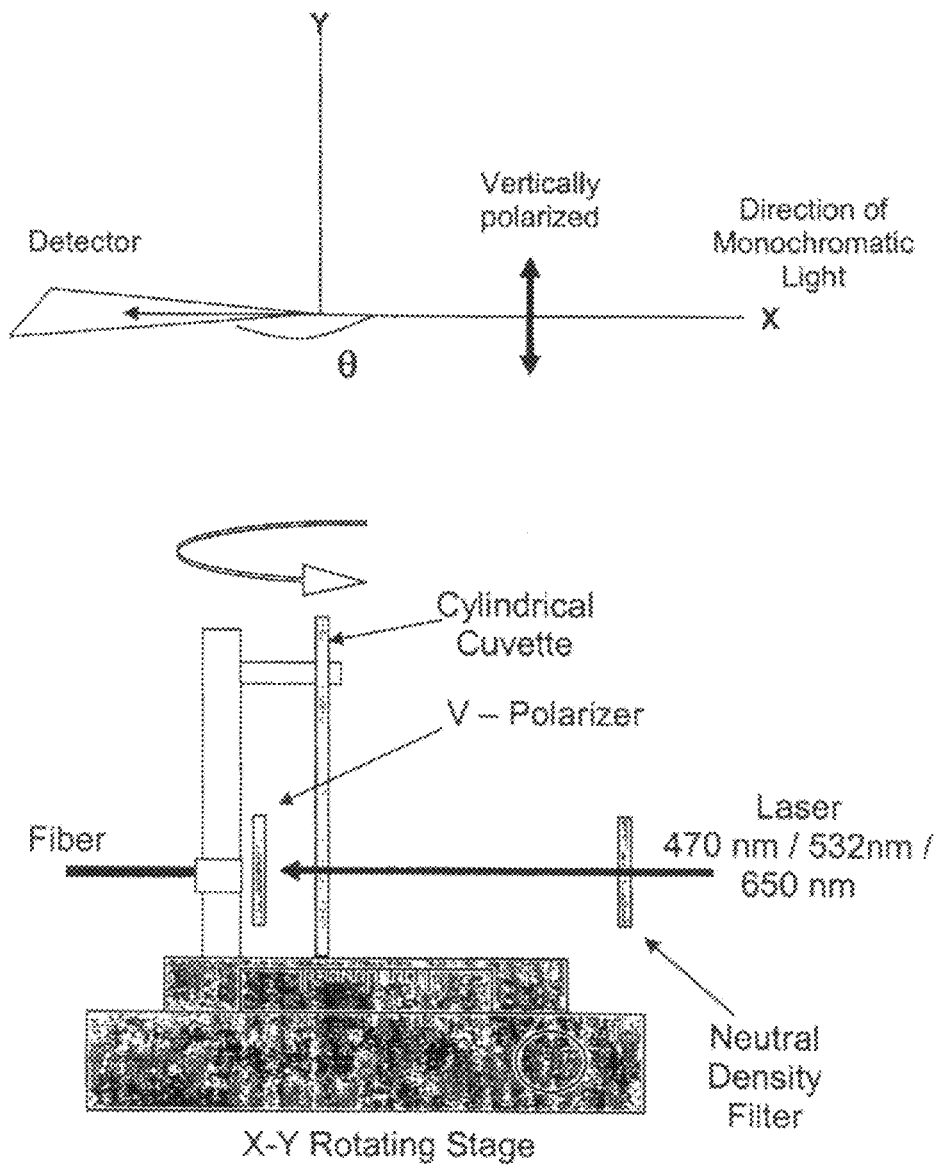
FIG. 1 shows a schematic of the system used to describe the geometrical arrangement of the illumination and detection systems (Top), and the apparatus used for measuring the polarized angular dependence of colloidal scatter (Bottom).

The present invention relates to affinity biosensing using polarization of light scattering from of aggregated noble metallic nanostructures to determine concentration of an analyte in a sample. This new sensing system utilizes the changes in polarized scattering from very small nanostructures, as compared to the changes in scattering observed by much larger aggregates of the nanostructures, due to a receptor-ligand binding reactions.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, or infection to be assayed.

The term "biological agent" means any molecule occurring in nature or a derivative of such a molecule. Exemplary biological agents may include nucleic acids, aromatic carbon ring structures, NADH, FAD, amino acids, carbohydrates, steroids, flavins, proteins, DNA, RNA, oligonucleotides, fatty acids, myoglobin, sugar groups such as glucose etc., vitamins, cofactors, purines, pyrimidines, formycin, lipids, phytochrome, phytofluor, lipids, antibodies and any type of cell.

This new model system can be potentially applied to many other nanoparticle assays and has many advantages over traditional fluorescence sensing and other light-scattering approaches. For example, a single nanoparticle can have the equivalent scattered intensity as $10^5$ fluorescing fluorescein molecules substantially increasing detection; the angular distribution of scattered light from noble metal colloids is substantially easier to predict as compared to fluorescence; the scattered light is not quenched by biospecies and the noble metal colloids are not prone to photo destruction, as is the case with organic fluorophores.

The present invention relates to affinity biosensing using plasmon light scattering emissions from interacting metallic nanostructures and measuring the polarization of such interacting metallic nanostructures during aggregation thereof.

The present invention also provides enhanced emissions using metallized nanostructures having elliptical, spherical, triangular, rod-like or any geometric form. In exemplary cases, the elliptical islands have aspect ratios of 3/2, and the spherical colloids have diameters of 20-60 nm. However, the invention is not limited to any particular geometry.

Light sources used for applying electromagnetic energy can include any source that may apply the necessary frequency or wavelength such as arc lamps, lasers and LCD sources. Detectors can include photomultiplier tubes. Additionally, it is advantageous for the device to have a monochromator so that specific wavelengths of light may be used to excite a molecule or to detect emissions at a specific wavelength.

In one embodiment, the metallic nanostructures may be prepared by reduction of metal ions using various reducing agents, using technique known to one skilled in the art. For example, sodium hydroxide may be added to a rapidly stirred silver nitrate solution thereby forming a precipitate.

Colloids can be prepared as suspensions by citrate reduction metals. Preferred metals are silver and gold. Again, gold may be used because of the absorption of gold at shorter wavelengths. The size of the colloids and their homogeneity can be determined by the extensive publications on the optical properties of metal particles available and the effects of interface chemistry on the optical property of colloids.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

The majority of sensors based on the nanoparticle surface plasmon resonance have been solution based, where the sensitivity of the sensors is typically determined by the sensitivity of the surface plasmons themselves to interparticle coupling.[24] When many particles, all supporting a surface plasmon resonance, are in close proximity, then they are able to interact electromagnetically through a dipole-dipole coupling mechanism. This mechanism, which can occur up to two and half times the diameter of the particles,[26] broadens and redshifts the plasmon resonance bands, where smaller clusters of particles have similar plasmon resonance properties as compared to that of a larger single particle. This has primarily lead to two main solution sensing formats using the nanoparticles, namely absorption/colorimetrically based,[25] and those which look for changes in plasmon light scattering properties. Intuitively, these properties can be considered as a function of the nanoparticle's cross section, $C_{ext}$, which is comprised of both absorption, $C_{abs}$, and scattering, $C_{sca}$, components, where $$C_{ext} = C_{sca} + C_{abs} \tag{1}$$

In addition to these two properties of nanoparticles, several other properties are known, but have been ill explored for biosensing. The present invention utilizes plasmon light scattering to develop the concept of angular-dependent polarization-based plasmon light scattering for bioaffinity sensing. Here, the excitation is perpendicular to the scattering plane and so no $\cos^2 \theta$ angular dependence of scatter is evident while the particles remain in the Rayleigh limit, i.e., diameter <1/20th $\lambda$. Subsequently, small Rayleigh like particles, with an initial polarization approaching unity, aggregate together via a bioaffinity reaction. The induced aggregation changes the spatial distribution of polarized scatter around the sample. However, to maximize the observed signal and therefore downstream the sensitivity of the assay, particles which initially scatter light in a Rayleigh dependence are preferably selected. Upon aggregation, an increased forward scatter is observed (particles now scattering in the Mie limit), enabling large changes in polarization to be subsequently observed at angles approaching 180°, the angle of forward scatter.

For the case where the incident light is polarized perpendicular to the scattering plane, then the extent of polarization, P, at any angle $\theta$ is given by the expression $$P = \frac{I_{PERP} - I_{PAR}}{I_{PERP} - I_{PAR}}, \tag{2}$$

where $I_{PERP}$ and $I_{PAR}$ are the scattered intensities in the perpendicular and parallel planes respectively. P can be positive or negative and $|P| \leq 1$. For plane polarized light, the plasmon scattered light by a homogeneously sized and dilute solution approaches 1. For light vertically polarized and perpendicular to the scattering plane, then the intensity of scatter is given by the well-known form of the Rayleigh expression $$I_{scatt} = \frac{16\pi^4 a^6 n_{med}^4 I_0}{r^2 \lambda^4} \left| \frac{m^2 - 1}{m^2 + 2} \right|^2, \tag{3}$$

where $I_0$ is the incident intensity of monochromatic light, $n_{med}$ is the refractive index surrounding the particle, m is the refractive index of the bulk particle material, and r is the distance between the particle and where the scattered light is detected. Here, there is no angular dependence of scatter. In the case where the excitation polarization is parallel to the scattering plane, then the scattering intensity for small homogeneous spherical particle with radius a, that is much smaller than the wavelength, $\lambda$, of the incident beam, is given by a slightly different form of the Rayleigh expression $$I_{scatt} = \frac{16\pi^4 a^6 n_{med}^4 I_0}{r^2 \lambda^4} \left|\frac{m^2-1}{m^2+2}\right|^2 \cos^2\vartheta. \quad (4)$$

In this condition, a $\cos^2\theta$ angular dependence of scatter is observed in the scattering plane. The intensity is highest at the observation angles 0° and 180° and minimum at 90° and 270° and is proportional to $\cos^2\theta$ at all other angles. The present invention employs excitation polarization perpendicular to the scattering plane, Equation 3, where no Rayleigh angular dependence of scattering occurs, the angular dependence due to particles scattering in the Mie limit after aggregation, which manifests itself in a increased forward scattering, i.e., at 180°.

When a metallic nanoparticle is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this reradiation of light at the same incident wavelength, which is often referred to as plasmon scatter. The scattering of light by very small subwavelength sized particles, is well described by Rayleigh theory. However, for larger particles, where the size of the nanoparticle is ~greater than $\frac{1}{20}^{th}$ the wavelength of light, or for Rayleigh sized particles in close proximity to one another, the scattering properties no longer obey Rayleigh theory, but indeed can be described by Mie's theory.

It is informative to briefly describe why the scattering from larger particles is no longer described by Rayleigh theory. It was previously mentioned that when a small particle is exposed to an electromagnetic field, whose wavelength is much larger than the diameter of the particle, then the electrons in the nanoparticle all sense the same phase of the incident wave, and therefore all scatter light with the same phase. In essence, the whole particle behaves as a large oscillating dipole moment, a function of the collective electron oscillations (plasmons). However, for much larger particles then the electrons on the particles can experience different phases, and therefore can oscillate with different phases. This inherently leads to interference of the light, which is scattered by the electrons from different parts of the particles. Subsequently, both the magnitude and angular distribution of the scattered light deviate from that expected of a normal oscillating electric dipole. The Mie theory for light scattering from large particles can be considered as light radiating from oscillating electric dipoles, as well as magnetic dipoles, quadruples and other higher order magnetic multipoles. Scattered light by Mie theory is well known and described by the following equation;

$$I_{scatt} = \frac{2\pi}{k^2} \sum_{n=1}^{\infty} (2n+1)(|a_n|^2 + |b_n|^2)$$

where $k=2\pi n_{med}/\lambda$. One can envision the different terms in the sum as corresponding to different electric and magnetic multipoles and n is the term index. The term with n=1 corresponds to the electric dipole. The coefficients an and bn are defined in terms of the Bessel and Ricatti functions and in general are complex numbers depending on whether the refractive index of the particle is real or complex[6]. When the particle is much smaller than the wavelength of light, the most important expression in the Mie equation becomes that of the electric dipole, and then the Mie equation reduces back to the Rayleigh expression.

The polarization of scattered light from different sized colloids allows the quantitative measurement of the concentration of receptor-ligand binding/or the level of receptors by the amount of ligand binding thereto. In one embodiment, the ligand is fused to a noble metal nanostructure, wherein the ligand binds to receptors on a biological tissue thereby induces nanoparticle aggregation. Thus, this polarized light scattering approach for bioaffinity sensing, will serve as a model system which could readily be applied to the many other nanoparticle assays which have been developed.

Figure 2:
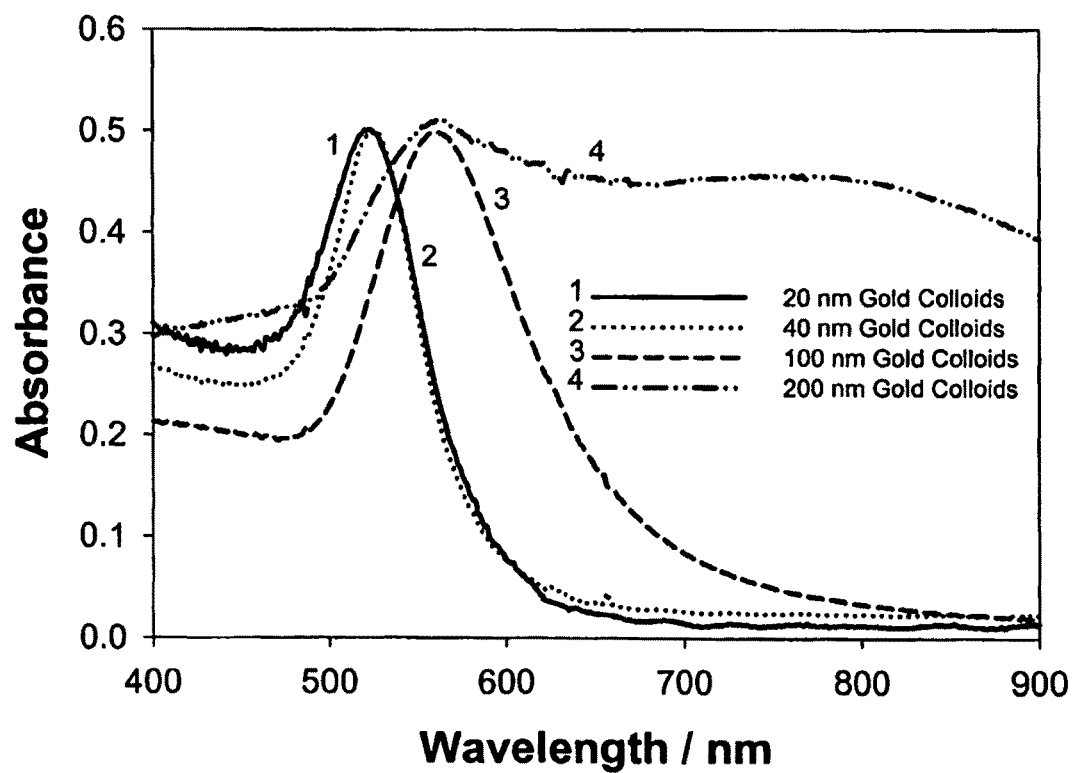
FIG. 2 shows the normalized absorption spectra of different sized gold colloids.

To demonstrate the present sensing approach, whereby the polarization of plasmonic scatter changes upon colloidal aggregation induced by a bioaffinity reaction, the polarized scattering behavior of uncoated gold colloid suspensions was initially studied. FIG. 2 shows the normalized absorption spectra of different sized gold colloids in citrate buffer. It can be clearly seen that the plasmon absorption band at 520 nm for 20 nm colloids, shifting red, as well as broadening as a function of size. Subsequently, for the polarized angular scattering dependency discussed herein, monochromatic laser light at 470, 532 and 650 nm was used because these frequencies are similar to the plasmon absorption maxima of the colloids.

Figure 3:
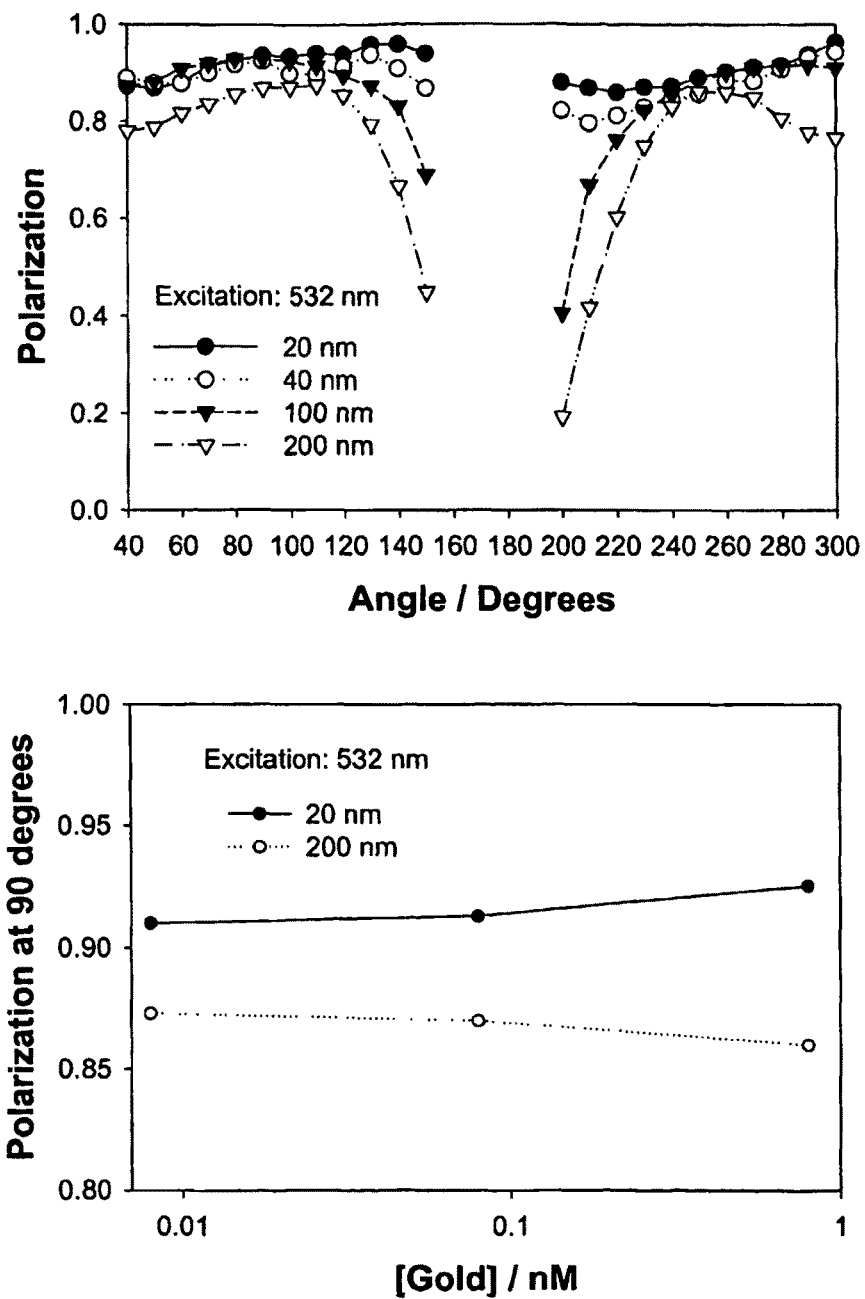
FIG. 3 shows the angular dependent-polarized scatter from different sized gold colloids (Top), and the polarization at 90 degrees for different concentrations of both 20 and 200 nm colloids (Bottom).

For bioaffinity sensing based on the polarized angular dependence of plasmon scatter, it is important to understand the concentration dependence of the colloids on the scattering spatial distribution. FIG. 3 shows the angular dependent-polarized scattering profiles for different sized colloids using 532 nm monochromatic laser light. As the colloids increase in size, there is a reduction in polarization. As expected the two (2) sets of polarized scattering curves in FIG. 3—top are essentially mirror images of each other, and simply reflect the 0-180 and 180-360 degree regions, as the fiber optic detector is rotated around the samples, and detects polarization after laser light passes through the sample and vertical polarizer as shown in FIG. 1—bottom.

FIG. 3—top shows the angular dependence of polarization of 532 nm plasmon-scattered light for a range of gold colloid sizes. The plot starts at a 40° view point, and ends with polarization values at 300° with respect to an excitation angle of 0°. Angles outside these ranges were not measurable due to the physical constraints of the rotational stage and the collection fiber positioning. From FIG. 3 it was observed that the plasmon-scatter polarization curves were almost symmetrical around the 180° angle, the slight nonsymmetries due to the exact positioning of the excitation beam in the center of the sample. Of particular interest is the sharp drop in polarization at angles approaching 180°, and also as a function of colloid size.

This interesting observation, which inevitably lends itself to an approach for bioaffinity sensing, can be explained in two ways. First, when a small particle is exposed to an electromagnetic wave whose wavelength is much longer than the diameter of the particle, then every electron in the metallic particle oscillates with the same phase as the wave, and therefore scatters light with the same phase. However, for larger particles when its diameter approaches the wavelength, then electrons in different parts of the particles oscillate with different phases. This leads to interference of the scattered light, sometimes referred to as dephasing,[27,28] where the both the intensity and angular distribution of the scattered light can be significantly different from that of smaller particles. In FIG.

3, at angles close to 180°, a decreased polarization for increased colloid size at a given angle was noticed and attributed to the dephasing of the scattered light. Second, the magnitude of these polarization changes is manifested in the fact, that greater scattered intensities are observed for an oscillating dipole at angles approaching 180°, i.e., the spatial distribution of scatter increases in the forward direction as a function of size. In this regard, initial unaggregated gold nanoparticles were chosen whose diameters are less than 1/20th the wavelength of light, i.e., Rayleigh scatterers, which upon aggregation no longer scatter light in a Rayleigh manner. Rayleigh theory applies quite strictly to particles for which the radius $a<<<\lambda/(2\pi n_{med}|m|)$, where $n_{med}$ is the refractive index of surrounding the nanoparticle and m is the refractive index of the bulk particle itself. For the gold colloids discussed here |m| is usually not greater than 4. Subsequently, it was observed that for $|m|=4$, $\lambda=532$ nm and $n_{med}=1.33$, this expression yields ideal Rayleigh scatters of 15.9 nm. According to Yguerabide,[27] particles up to 40 nm diameter can still be considered to be in the Rayleigh limit for visible incident wavelengths.

From FIG. 3 it is also important to note that a drop in polarization at angles near 180° was noted, which can be considered to be the angle where one would normally expect a high polarization value due to unaffected incident light, cf. a solution of fluorophores. However, in the present system here, the solution optical density was ≈1. Subsequently only a very small fraction of the incident light does not interact with the colloids, which are well-known to interact and scatter light outside the constraints of their physical cross sections, when $Q_{sca}>1$, and where $Q_{sca}=C_{sca}/\pi a^2$, and $Q_{sca}$, is the scattering efficiency, a is the particle radius, and $C_{sca}$, is the scattering cross section.

FIG. 3—bottom demonstrates this sensing strategy and shows a polarization plot at 90 degrees as a function of 20 nm and 200 nm gold colloid concentrations. The linearity of the plot shows that the concentration of the colloids does not change the spatial distribution of the scatter, which is a most important consideration for sensing applications. In addition, the concentration range studied, typically reflects that used in colloidal plasmon absorption type biosensing assays. Importantly, there is a noticeable difference in the polarization in the different sized colloids, that being as the colloid size increases, polarization decreases.

Figure 4:
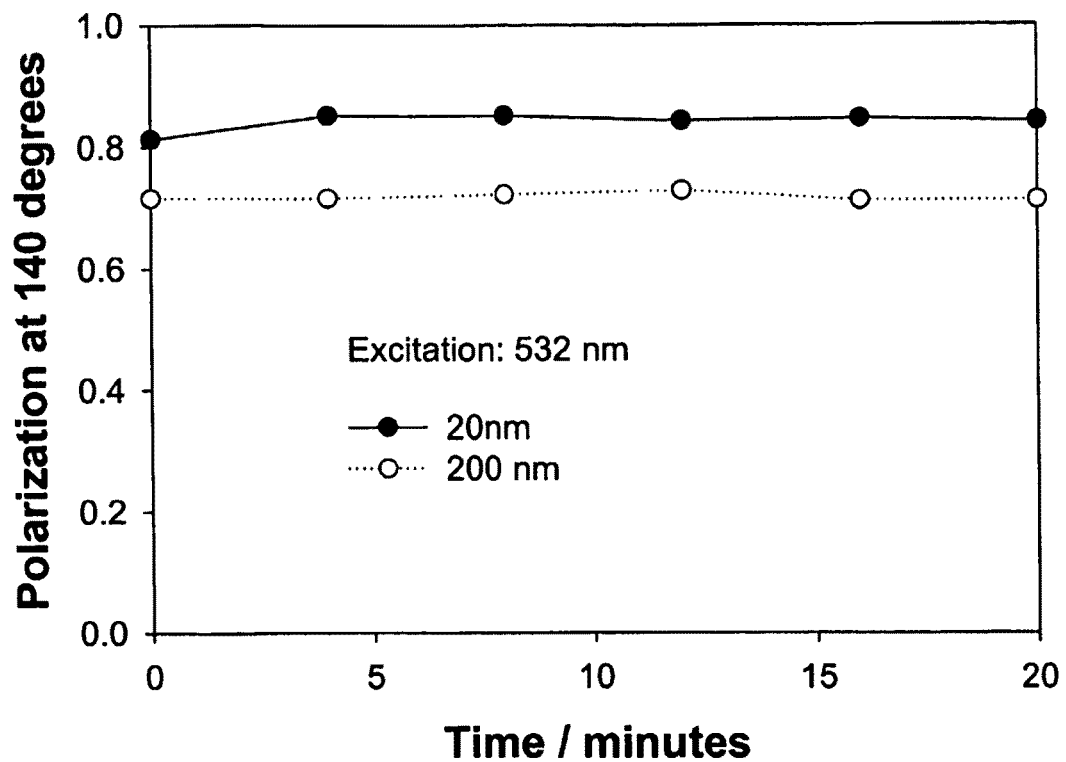
FIG. 4 shows graphically "Polarization Vs Time" for different sized gold colloids.

FIG. 4 shows the polarized scattering from 20 nm and 200 nm at 532 nm laser light and at 140 degrees. Again, it is evident that the polarization decreases as the colloid size increases. Further, the linearity of the plot shows that time does not change the spatial distribution of the polarization. Clearly, this plot shows the colloidal size dependence of polarized-scattering at a given incident wavelength. Subsequently, by viewing the polarization at 90 and 140 degrees as a function of gold colloid size in FIGS. 3 and 4, it can be seen how the size distribution of polarization is changing. For small colloids, the polarization is greater than that of the larger colloids.

For the presently described bioaffinity sensing scheme, the initial gold colloid size was chosen so that it would be in the Rayleigh limit, i.e. 20 nm. Upon protein-induced aggregation of the colloids, the scattering distributions become increasingly more complex as a function of protein addition, the scattering no longer following a Cos 2θ dependence. Similar to the unmodified colloids, the polarization changes, and can subsequently be correlated with protein concentration, or indeed any analyte or biospecies which can induced colloidal aggregation. Importantly, the dynamic range of the sensing strategy manifests itself in being able to aggregate particles that initially scatter in the Rayleigh limit, into the Mie limit after aggregation, c.f. the range shown in FIG. 6.

Finally, to investigate both the photostability of the colloids, as well as to ascertain whether the colloids would settle out of solution as a function of time, the polarized scattering was monitored as a function time using 532 nm incident light measured at 140 degrees and shown in FIG. 4. For all colloid sizes, it was found that the relative polarization remained constant over the 20 minute measurement period. This was particularly encouraging and demonstrates that both the colloids do not settle from solution during measurements, and that the laser powers employed (several mW) do not alter the shape of the colloids, as has been reported by some authors, but for higher incident laser powers.[23] From FIG. 4, it can be seen that the colloids are photostable, more so than traditional fluorophores, which are prone to photo degradation,[22] their scattering distributions not changing as a function of time.

Figure 5:
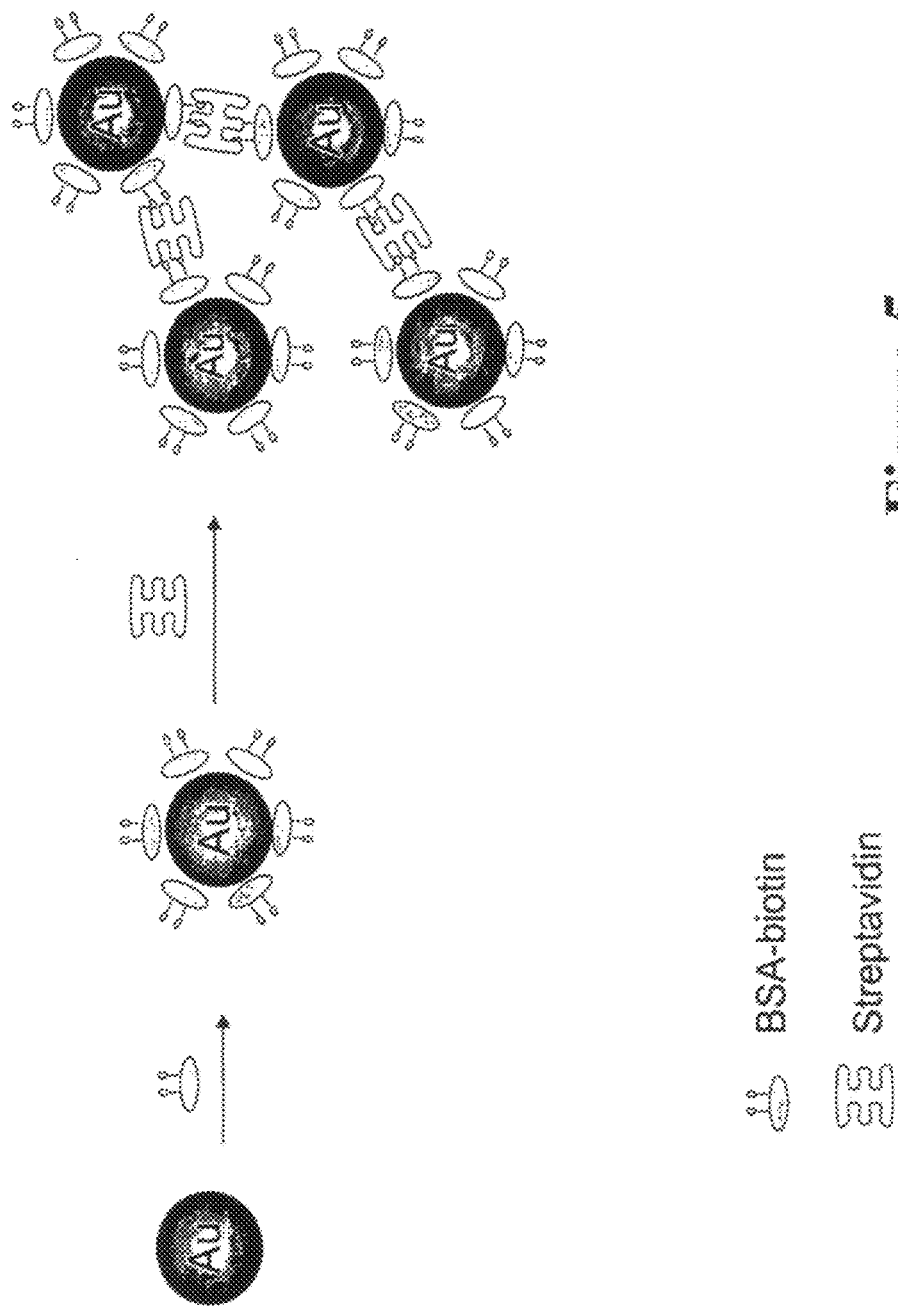
FIG. 5 shows a model system (BSA-Biotin colloids crosslinked by steptavidin) to demonstrate the utility of polarized angular plasmon-resonance based light scattering for affinity biosensing or imaging.

To demonstrate the utility of the described system, a model protein system was chosen as shown in FIG. 5. Biotinylated bovine-serum albumin-coated 20 nm colloids (BSA-colloids) can be readily prepared, which cluster by the addition of the tetravalent protein streptavidin,[19] and the association of biotin and streptavidin is very strong,[19] eliminating the possibility of back disassociation reactions to complicate our model system's kinetics. The streptavidin-biotin system has been widely used for demonstration of nanoscale bioaffinity sensors, primarily due to the extremely high binding affinity, $K_d \approx 10^{13}$ 1/M. Streptavidin is a tetrameric protein, which can bind up to four biotinylated molecules. Subsequently streptavidin can be used to crosslink biotinylated-bovine serum albumin (BSA) coated 20 nm gold colloids, in essence causing the near-field plasmon coupling of the nanoparticles, a subsequent change in their polarization (a function of colloidal proximity) as well as breaking the Rayleigh scattering limit, the particles upon aggregation starting to scatter in the Mie limit.

The surface modification of 20 nm gold colloids was performed using a modified version[29] of the procedure found in the literature.[30] The biotinylated-BSA colloids were used in the aggregation assays with increasing concentrations of streptavidin. In this regard, a 1000 nM stock solution of streptavidin (prepared in polybutene sulfone based on the specifications provided by manufacturer, Sigma/Aldrich, E1% at 282 nm=31.0) was added to 0.5 mL of biotinylated gold colloid samples and incubated at room temperature for 30 min. In order to achieve the desired final streptavidin concentrations, predetermined volumes of streptavidin stock solution were used. The angle-dependent polarized scattering from gold colloids of various sizes and those used in the aggregation assay were measured using an X-Y rotating stage (Edmund Optics), that was modified to hold a cylindrical cuvette (a thin walled glass NMR tube), with a fiber optic mount. (FIG. 1)

The gold colloids were illuminated with a 532 nm laser line, a neutral density filter being used to adjust the laser intensity. The angle-dependent polarized scattered light from the gold colloids was collected through a dichroic sheet polarizer (Edmund optics) into a 600 micron broad wavelength fiber that was connected to an Ocean Optics HD2000 spectrofluorometer.

Figure 6:
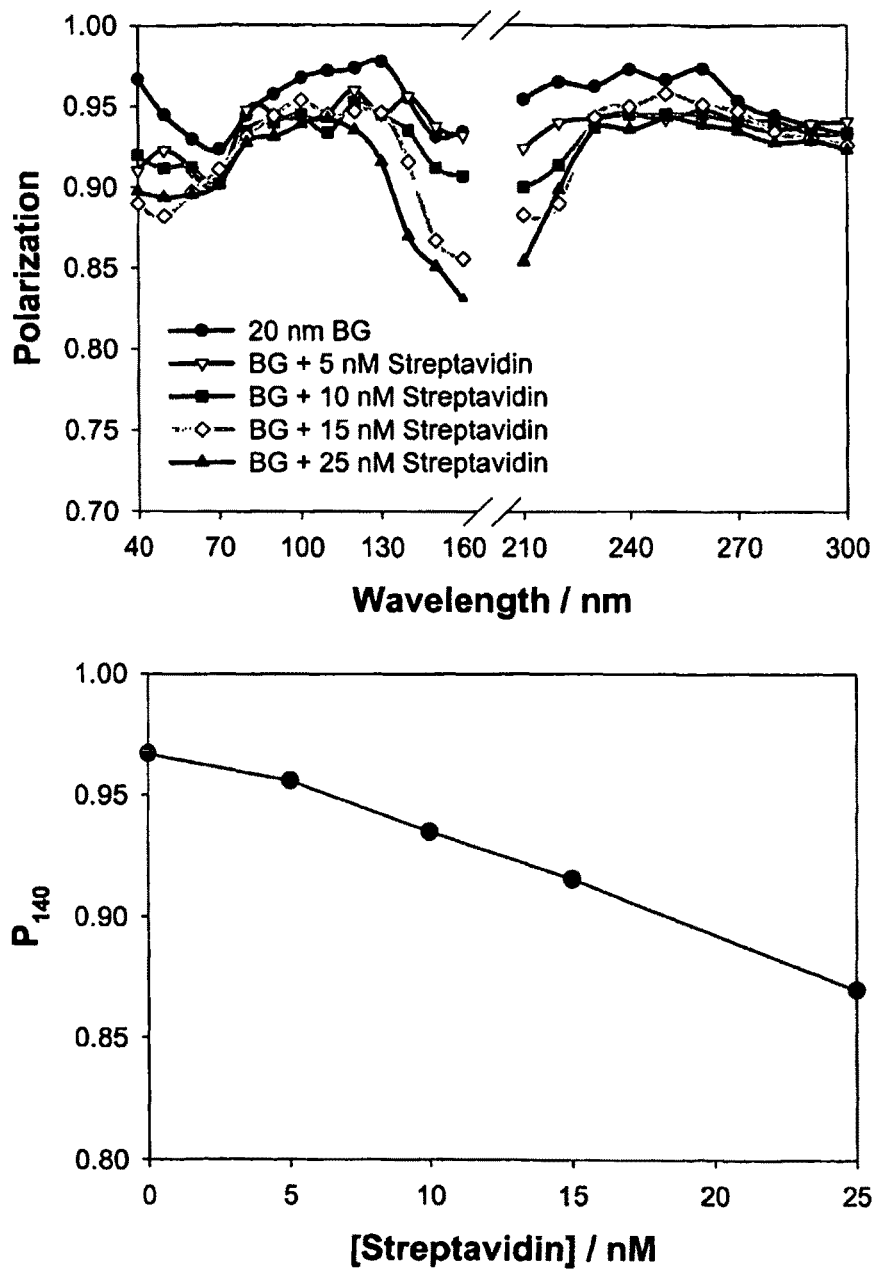
FIG. 6 shows the angular-dependent polarization of plasmon scatter as a function of nanoparticle aggregation (Top), and the polarization, P, at 140 degrees Vs streptavidin concentration (Bottom). BG—Biotinylated gold colloids.

Similar to the polarization measurements of the virgin colloids as a function of colloidal size, the 20 nm biotinylated-BSA coated gold particles showed a substantial decrease in polarization at an angle approaching 180° upon increasing additions of streptavidin, FIG. 6—top. This decrease is explained as due to the near-field coupling of surface plasmons upon aggregation, which results in dephased polarized scatter similar to the effect observed for increasing colloid size, i.e., FIG. 3—top. As the concentration of streptavidin in the sample increases, an increase in the width of the scatter band at 180° was observed, i.e., an increase in the extent of forward scatter as the aggregated particles no longer scatter within the Rayleigh limit, but indeed now begin to scatter light as described by Mie theory. Subsequently the concentration of steptavidin can be readily determined, FIG. 6—bottom, as could any other biospecies which induces particle flocculation.

Figure 7:
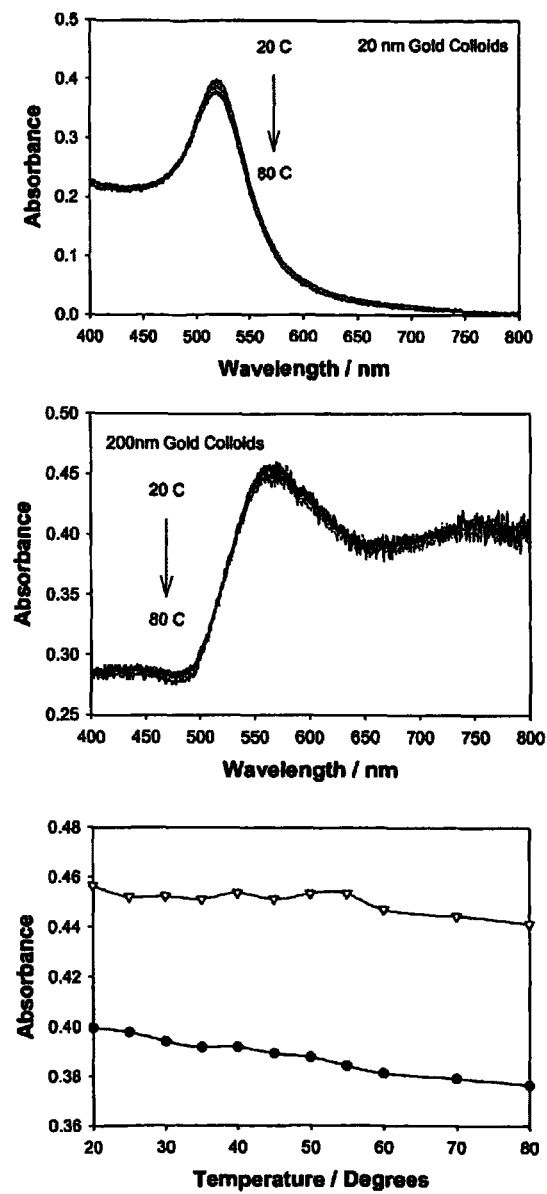
FIG. 7 shows the temperature dependent changes in the plasmon absorption of gold colloids.

FIG. 7 shows the temperature dependent changes in the plasmon absorption of gold colloids. Clearly, the different sized colloids absorb at a different frequencies as shown earlier in FIG. 2 and as the temperature increases, the absorbency decreases slightly as shown in the bottom plot.

Figure 8:
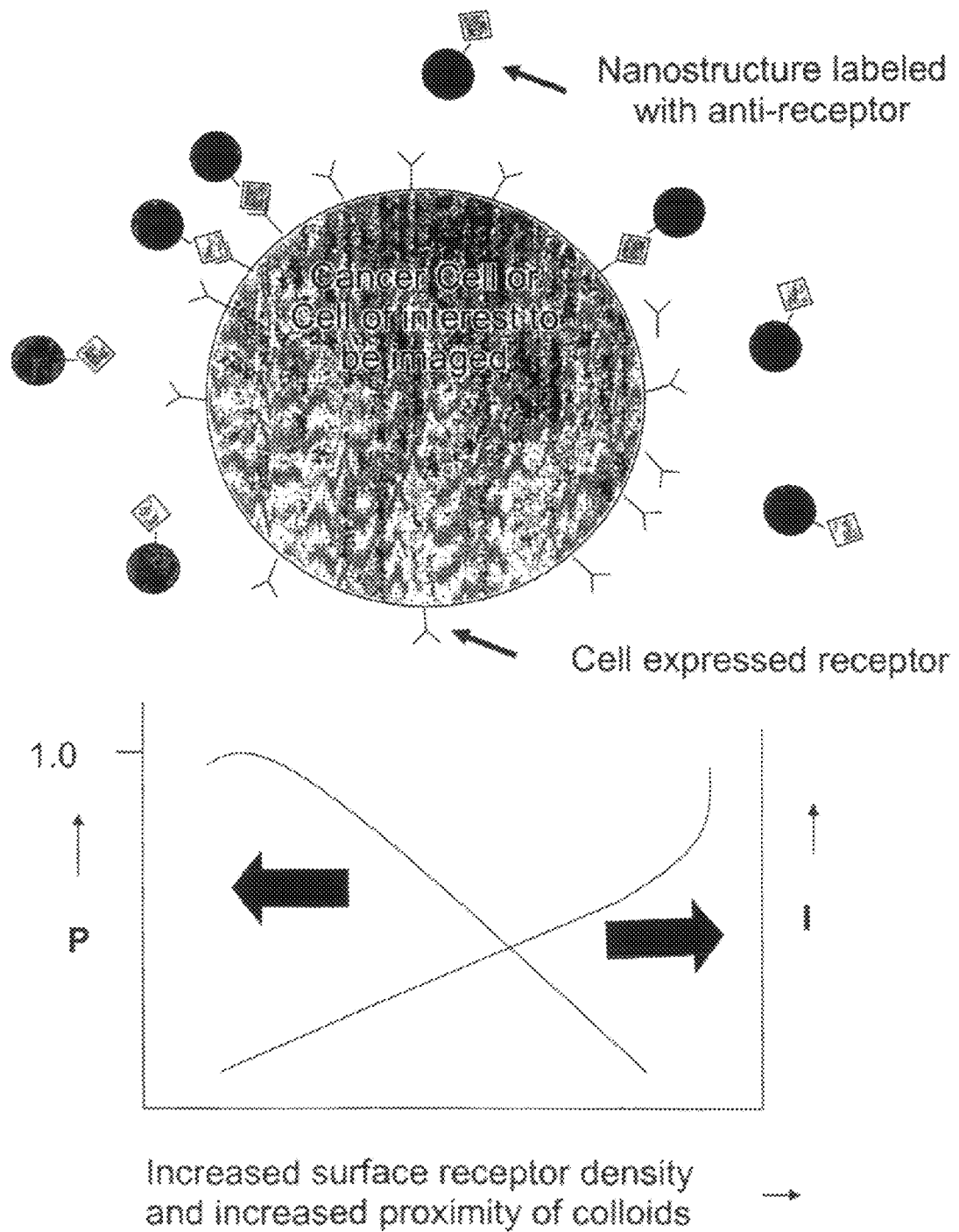
FIG. 8 shows the applicability of polarized based imaging to cancer detection/imaging and receptor density quantization. P—Polarization, I—Intensity of plasmon scatter at a unique wavelength.

FIG. 8 shows the applicability of polarized based imaging to cancer detection/imaging and receptor density quantization. P—Polarization, I—Intensity of plasmon scatter at a unique wavelength. Cancer cells are known to over express different proteins on their surface. Typically anti receptors can target these proteins and thus image cancer cells. However, using fluorescence, one only sees a decreased signal as the fluorophores bind to receptors in close proximity to each other. It is for this reason that no technique today allows for reliable quantization of cellular surface receptor density. The polarized scatter described here, indeed allows this to happen as the total scattered intensity is not perturbed by the close proximity of the nanostructures, and instead increases, while the polarization simply drops as shown in FIG. 8. In addition, this invention allows for possible drug delivery quantization to be monitored.

For the presently described bioaffinity sensing scheme, the initial gold nanostructure size was chosen so that it would be in the Rayleigh limit, i.e. within the range of 6 nm to 40 nm, and more preferably from about 20 nm to 30 nm. Upon affinity induced aggregation of the metallic nanostructures, the scattering distributions become increasingly more complex as a function of protein addition, the scattering no longer following a Cos 2θ dependence. Similar to the unmodified nanostructures, polarization changes, can subsequently be correlated with protein concentration, or indeed any analyte or biospecies which induces the nanostructure aggregation. Importantly, the dynamic range of the sensing strategy manifests itself in being able to aggregate particles that initially scatter in the Rayleigh limit, into the Mie limit after aggregation.

Notably, when the two metal nanostructures approach, the polarization of plasmonic scatter changes due to metal aggregation induced by a bioaffinity reaction. The difference of the polarization of the coupled plasmonic scatter is compared to a control for non-aggregated nanostructures and as the binding of ligand/analyte to the capture/receptor increases, the polarization decreases. Thus, this decrease in polarization can be used to determine the level of concentration of ligand/analyte when compared to a control system. As formation of the receptor-ligand-detector increases with aggregation of metallic nanostructures, the polarization decreases proportional to the concentration of a binding ligand.

Upon aggregation of the nanoparticles, the solution polarization rapidly decreases due to near-field plasmon coupling. Interestingly, by choosing particles that initially scatter incident light in a Rayleigh manner, the present inventor has been able to show that the spatial distribution of polarized scatter also changes upon particle aggregation as the particles now scatter in an increased forward direction (i.e. in the Mie limit). With an initial solution optical density of ≈1, significant depolarization occurs at angles greater than 140°, less than 220° and maximum around 180° from the incident excitation. Subsequently, this approach allows the determination of solution protein or analyte concentrations using polarized scatter, the dynamic sensing range determined by the angle of observation.

The polarized-scattering from metallic surfaces can be measured using an X-Y rotating stage (Edmund Optics), that was modified to hold a cylindrical cuvette (a thin walled NMR tube), with a fiber optic mount, as shown in FIG. 1. The metallic structures can be illuminated with vertically polarized laser sources with a neutral density filter being used to adjust the laser intensity. The angle-dependent vertically polarized scattered light from the metallic surfaces can be collected through a dichroic sheet polarizer (Edmund optics) into a 600 micron broad wavelength fiber that was connected to an Ocean Optics HD2000 spectrofluorometer. The photostability aggregation of metallic surfaces can be measured by simply observing the polarized scattered intensity at different angles, such as 90 or 140 degrees for a specific length of time, such as 30 or 45 minutes.

Notably, the present invention provides for the application of plasmon scatter and the measurement of distances in the range 10-300 nm for biological systems. Today, optical distance measurements less than 10 nm are undertaken using FRET between a fluorescent donor and an acceptor. Distances ranging from macroscopic to about λ/2, typically about 300 nm, can be measured using confocal, multiphoton and/or laser scanning methods but these systems are not readily compatible with biological species, such as live cells. This approach may be of significant importance for studying macromolecular dynamics and particularly in immunoassays, which typically have dimensions far too large for classical FRET.

Materials and Methods

Materials

Colloidal gold dispersions (20, 40, 100 and 200 nm) were purchased from Ted Pella. Glycerol, sodium phosphate monobasic, phosphate buffered saline (PBS), streptavidin, biotinamidocaproyl labeled bovine serum albumin (biotinylated BSA) and standard glass NMR tubes (5 mm, series 300) were purchased from Sigma-Aldrich. All chemicals were used as received.

Methods

Preparation of Biotinylated BSA-Coated 20 nm Gold Colloids

The surface modification of 20 nm gold colloids was performed using an adapted version of the procedure found in the literature.[19] In this regard, 5 mL of the gold colloid solution was mixed with 0.05 mL aqueous solution of biotinylated BSA (1.44 mg/ml), and this mixture was incubated at room temperature for 2 hours. The gold colloid/biotinylated BSA mixture was then centrifuged in an Eppendorf centrifuge tube equipped with a 100,000 MW cut-off filter for 10 minutes, using an Eppendorf microcentrifuge at 8,000 g, to separate the biotinylated BSA-coated gold colloids from the excess biotinylated BSA. The supernatant was carefully removed, and the pellet containing the biotinylated gold colloids was resuspended in 10 mM sodium phosphate buffer (pH 7). This was subsequently used in the aggregation assays.

Aggregation Assay Using Biotinylated Gold Colloids and Streptavidin

The model aggregation assay, used to demonstrate the utility of our approach, was performed by mixing biotinylated gold colloids (20 nm) with increasing concentrations of streptavidin in a quartz cuvette. In this regard, a 1000 nM stock solution of streptavidin (prepared in PBS based on the specifications provided by manufacturer, E1% at 282 nm=31.0) was added to 0.5 mL of biotinylated gold colloid samples and incubated at room temperature for 30 minutes. In order to achieve the desired final streptavidin concentrations, predetermined volumes of streptavidin stock solution were used. The degree of aggregation was measured by recording the absorption spectrum of each sample (as with all other absorption measurements), using a Varian Cary 50 spectrophotometer.

Aggregation Assay

The angle-dependent polarized-scattering from gold colloids of various sizes and those used in the aggregation assay were measured using an X-Y rotating stage (Edmund Optics), that was modified to hold a cylindrical cuvette (a thin walled NMR tube), with a fiber optic mount (FIG. 1—bottom). The gold colloids were illuminated with three different vertically polarized laser sources: 470, 532 and 650 nm, a neutral density filter being used to adjust the laser intensity. The angle-dependent vertically polarized scattered light from the gold colloids was collected through a dichroic sheet polarizer (Edmund optics) into a 600 micron broad wavelength fiber that was connected to an Ocean Optics HD2000 spectrofluorometer. The photostability of 20, 40 and 200 nm gold colloids, under constant illumination with a 532 nm laser, was measured by simply observing the polarized scattered intensity at different angles, such as 90 or 140 degrees for a specific length of time, such as 30 or 45 minutes.

In conclusion, this model sensing platform may be applied to many other nanoparticle assays. The present invention suggests that polarization based assays can be performed with a simple near-180° geometry detection of the scattered light, as compared to the total-internal reflection fluorescence or backscattered fluorescence geometries currently employed. Further, in the present invention, an assay "hit" could be determined by colloid proximity and not rotational orientation as is currently used to transduce polarization assays. In addition, the nanoparticles are inherently more photostable than fluorophores, do not settle out solution, and can couple over 2.5 times their diameter, enabling long-range plasmon coupling and therefore the sensing of large antigens.

REFERENCES

The contents of all cited references are hereby incorporated by reference herein for all purposes.
(1) Bryant, G;. Thomas, J. C. *Langmuir* 1995, 11, 2480-2485.
(2) Dahneke, B. E. Ed. *Measurements of Suspended Particles by Quasi-Elastic Light Scattering*, Wiley-Interscience, New York, 1983.
(3) Chu, B. *Laser Light Scattering*, 2nd Ed., Academic Press, New York, 1991.
(4) Brown, W. Ed. *Dynamic Light Scattering: The Method and Some Applications*, Clarendon Press, Oxford, England, 1993.
(5) Finay, R. *Adv. Colloid Interface Sci.* 1994, 52, 79-143.
(6) Yguerabide, J.; Yguerabide, E. *Anal. Biochem.* 1998, 262, 137-156.
(7) Yguerabide, J.; Yguerabide, E. *Anal. Biochem.* 1998, 262, 157-176.
(8) Aslan, K.; Lakowicz, J. R.; Geddes, C. D. *Anal. Chem.Acta.* 2004, 517, 139-144.
(9) Aslan, K.; Lakowicz, J. R.; Geddes, C. D. *Anal. Biochem.* 2004, 330, 145-155.
(10) Reynolds, R. A.; Mirkin, C. A.; Letsinger, R. L. *J. Am. Chem. Soc.* 2000, 122, 3795-3796.
(11) Elghanian, R.; Storhoff, J. J.; Mucic, R. C.; Letsinger, R. L.; Mirkin, C. A. *Science* 1997, 277, 1078-1081.
(12) Sastry, M.; Lala, N.; Patil, V.; Chavan, S. P.; Chittiboyina, A. G. *Langmuir* 1998, 14, 4138-4142.
(13) Cobbe, S.; Connolly, S.; Ryan, D.; Nagle, L.; Eritja, R.; Fitzmaurice, D. *J. Phys. Chem. B* 2003, 107, 470-477.
(14) Nath, N.; Chilkoti, A. *Anal. Chem.* 2002, 74, 504-509.
(15) Souza, G. R.; Miller, J. H. *J. Am. Chem. Soc.* 2001, 123, 6734-6735.
(16) Kerker, M. The Scattering of Light and Other Electromagnetic Radiation, Academic Press, New York, 1969.
(17) Mie, G. *Ann. Phys.* 1908, 25, 377-445.
(18) Collier, C. P.; Vossmeyer, T.; Heath, J. R. *Annu. Rev. Phys. Chem.* 1998, 49, 371-404
(19) Roll, D.; Malicka, J.; Gryczynski, I.; Gryczynski, Z.; Lakowicz, J. R. *Anal. Chem.* 2003, 75, 3108-3113.
(20) Mayes, A. G.; Blyth, J.; Millington, R. B.; Lowe, C. R. *Anal. Chem.* 2002, 74, 3649-3657.
(21) Kim, Y.; Johnson, R. C.; Hupp, J. T. *Nano Lett.* 2001, 1(4), 165-167.
22) Lakowicz, J R. Principles of Fluorescence Spectroscopy; Kluwer/Academic Plenum Publishers: New York, 1997.
(23) Millard, M.; Huang, P.; Brus, L. *Nano Lett.* 2003, 3, 1611-1615.
(24) D. A. Stuart, A. J. Haes, C. R. Yonzon, E. M. Hicks, and R. P. Van Duyne, IEE. Proc.-Nanobiotechnol. 152, 13 (2005).
(25) E. Hutter and J. H. Fendler, Adv. Mater. (Weinheim, Ger.) 16, 1685 (2004).
(26) K.-H. Su, Q.-H. Wei, X. Zhang, J. J. Mock, D. R. Smith, and S. Schultz, *Nano Lett.* 3, 1087 (2003).
(27) J. Yguerabide and E. Yguerabide, *Anal. Biochem.* 262, 137 (1998).
(28) J. Yguerabide and E. Yguerabide, *Anal. Biochem.* 262, 157 (1998).
(29) K. Aslan, P. Holley, L. Davies, J. R. Lakowicz, and C. D. Geddes, *J. Am. Chem. Soc.* 127, 12115 (2005).
(30) R. A. Reynolds, C. A. Mirkin, and R. L. Letsinger, *J. Am. Chem. Soc.* 122, 3795 (2000).

That which is claimed is:

1. A bioassay for measuring concentration of a binding couple by measuring changes in polarization values due to changes in polarized scattered light emitted from metallic nanostructures, the method comprising:
   a) preparing metallic nanostructures comprising a multiplicity of one member of the binding couple having an affinity for the other member of the binding couple contained in a test sample, wherein the other member of the binding couple in the test sample binds to multiple metallic nanostructures, wherein the metallic nanostructures are sized to scatter light according to the Rayleigh scattering theory and range from 6 nm to 40 nm, wherein the metal supports plasmonic emissions and is selected from the group consisting of silver, gold, platinum, copper and combinations thereof;
   b) contacting the metallic nanostructures with the test sample;
   c) exposing the metallic nanostructures to electromagnetic radiation at a frequency that is scattered by the metallic nanostructures;
   d) detecting the polarization of scattered light emitted from the metallic nanostructures at a specific angle; and
   e) measuring the polarization of scattered light for a sufficient time to determine a changing polarization value, wherein the polarization value is decreased as the aggregation of metallic nanostructures increases due to increased binding of the member of the binding couple in the test sample binds to multiple metallic nanostructures.

2. The method according to claim 1, wherein the metallic nanostructures are any geometrical shape.

3. The method according to claim 2, wherein the geometric shape is spherical, triangular, elliptical, rod shape, hexagonal or the multifaceted.

4. The method according to claim 1, wherein the metallic nanostructures further comprise a substrate core fabricated of glass and/or a polymeric material.

5. The method according to claim 1, wherein the polarization of scattered plasmon emissions is measured at different angles or different wavelength to determine the changes in polarization relative to changes in the distances between metallic nanostructures.

6. The method according to claim 1, wherein the metallic nanostructures have a cross-section from about 20 nm to about 30 nm.

7. The method according to claim 1, wherein the binding couple is a receptor-ligand binding couple.

8. The method according to claim 7, wherein the receptor is positioned on a cancer cell.

9. A biosensing method for measuring concentration of an analyte in a test sample by measuring changes in polarization values due to changes in polarized scattered light emitted from metallic structures, the method comprising:
   a) providing metallic nanostructures having multiple binding probes for binding with at least two of the analyte in the test sample, wherein the size of the metallic nanostructures is from 20 nm to 30 nm and sized to scatter light according to the Rayleigh scattering theory;
   b) contacting the metallic nanostructures with the test sample;
   c) exposing the metallic nanostructures to electromagnetic radiation at a frequency that is scattered by the metallic nanostructures;
   d) detecting the polarization of scattered light emitted from the metallic nanostructures at an angle of detection from 190 to 220 or 140 to 160 with respect to an excitation angle of 0° along the X axis; and
   e) measuring the change in polarization of plasmonic scattered light emitted from metallic nanostructures for a sufficient time to determine a change in polarization values wherein a decrease in polarization value is due to a decrease in the polarization of scattered light as aggregation occurs between the metallic nanostructures due to binding of the analyte to multiple metallic nanostructures.

10. The method according to claim 9, wherein the analyte is a cancer cell having a surface binding location for the probe.

11. The method according to claim 9, wherein the metallic nanostructures comprise at least one noble metal.

12. The method according to claim 9, wherein the metallic nanostructures are any geometrical shape.

13. The method according to claim 12, wherein the geometric shape is spherical, triangular, elliptical, rod shape, hexagonal or the multifaceted.

14. The method according to claim 9, wherein the metallic nanostructures are fabricated from any metal that support plasmonic emissions.

15. The method according to claim 14, wherein the metal is silver, gold, platinum, copper and/or combinations thereof.

16. A bioassay for measuring concentration of receptor-ligand binding by measuring changes in polarization values due to changes in polarized scattered light emitted from noble metallic nanostructures, the method comprising:
   a) preparing a metallic sensing structure by attaching ligands to a noble metallic nanostructure wherein the ligands have affinity for a receptor on biological tissue, wherein the noble metallic nanostructure is sized to scatter light according to the Rayleigh scattering theory and range from 6 nm to 40 nm;
   b) contacting a sample suspected of containing the biological tissue with the metallic sensing structures, wherein the receptors on the biological tissue will bind to ligands attached to at least two noble metallic nanostructures;
   c) exposing the sample and metallic sensing structures to electromagnetic radiation at a wavelength that is scattered by the metallic structures;
   d) measuring the polarization of scattered light emitted from metallic nanostructures at a specific angle that provides a polarization value for monitoring aggregation due to binding of receptors to ligands on multiple metallic nanostructure, wherein the polarization value is decreased as the ligands attached to the metallic nanostructures bind to the receptors on the biological tissue increases.

17. The method according to claim 16, wherein the measuring of the polarization is conducted for at least 30 minutes.

18. The method according to claim 16, wherein the polarization of scattered plasmon emissions is measured at different angles or different wavelength to determine the changes in polarization relative to changes in the distances between metallic nanostructures.

19. The method according to claim 18, wherein the angle of detection measurement is from about 190 to about 220 or from about 140 to about 160 with respect to an excitation angle of 0° along the X axis.

20. The method according to claim 16, wherein the biological tissue is a cancer cell.

* * * * *